(12) United States Patent
Akagi et al.

(10) Patent No.: US 8,709,329 B2
(45) Date of Patent: Apr. 29, 2014

(54) MEDICAL CAPSULE HOUSING FORMED BY THERMAL WELDING

(75) Inventors: Toshimasa Akagi, Tokyo (JP); Hidetake Segawa, Tokyo (JP)

(73) Assignee: Olympus Corporation (JP)

( * ) Notice: Subject to any disclaimer, the term of this patent is extended or adjusted under 35 U.S.C. 154(b) by 278 days.

(21) Appl. No.: 13/080,999

(22) Filed: Apr. 6, 2011

(65) Prior Publication Data

US 2011/0180197 A1 Jul. 28, 2011

Related U.S. Application Data

(62) Division of application No. 11/483,050, filed on Jul. 7, 2006, now Pat. No. 7,931,584.

(30) Foreign Application Priority Data

Jan. 7, 2004 (JP) ................................. 2004-002424
Mar. 16, 2004 (JP) ................................. 2004-075066

(51) Int. Cl.
*B29C 65/08* (2006.01)

(52) U.S. Cl.
USPC ........................................................ 264/445

(58) Field of Classification Search
USPC ......................................... 264/445; 156/73.1
See application file for complete search history.

(56) References Cited

U.S. PATENT DOCUMENTS

| | | | |
|---|---|---|---|
| 3,973,064 A | 8/1976 | Paine | |
| 4,281,763 A | 8/1981 | Pace | |
| 4,543,138 A * | 9/1985 | Bollinger et al. | ............... 156/69 |
| 4,738,817 A | 4/1988 | Wittwer et al. | |
| 5,006,117 A | 4/1991 | Cassou | |
| 5,482,008 A | 1/1996 | Stafford et al. | |
| 5,540,808 A | 7/1996 | Vincent | |

(Continued)

FOREIGN PATENT DOCUMENTS

| | | |
|---|---|---|
| EP | 0 180 543 | 5/1986 |
| JP | 53-49877 A | 5/1978 |

(Continued)

OTHER PUBLICATIONS

English abstract of JP02059170.*

(Continued)

*Primary Examiner* — Larry Thrower
*Assistant Examiner* — Xue Liu
(74) *Attorney, Agent, or Firm* — Ostrolenk Faber LLP

(57) ABSTRACT

A capsule-type medical apparatus includes a distal-end cover which is formed in a substantially hemispherical dome shape, the distal-end cover having an open bonding end portion; a drum portion cover which is formed in a hollow cylindrical shape, the drum portion cover having an open bonding end portion; a function executing unit which executes a predetermined preset function, the function executing unit being accommodated in the drum portion cover; and an electric storage unit which accumulates drive electric power for driving the function executing unit, wherein the bonding end portion of the distal-end cover and the bonding end portion of the drum portion cover are subjected to a surface treatment, the bonding end portion of the distal-end cover and the bonding end portion of the drum portion cover are bonded after the surface treatment to form an outer casing which has a capsule shape insertable into a test subject and which seals an inside in a liquid tight manner.

3 Claims, 11 Drawing Sheets

(56) References Cited

U.S. PATENT DOCUMENTS

| | | | |
|---|---|---|---|
| 5,641,510 | A | 6/1997 | Clark |
| 5,725,477 | A | 3/1998 | Yasui et al. |
| 5,731,957 | A | 3/1998 | Brennan |
| 5,993,378 | A | 11/1999 | Lemelson |
| 7,037,393 | B2 | 5/2006 | Drummond |
| 7,163,693 | B1 | 1/2007 | Clarke |
| 2002/0103417 | A1 | 8/2002 | Gazdzinski |
| 2003/0029558 | A1 | 2/2003 | Hochrainer |
| 2003/0030180 | A1 | 2/2003 | Meek et al. |
| 2003/0068369 | A1* | 4/2003 | McAllister et al. ........... 424/465 |
| 2003/0181794 | A1 | 9/2003 | Rini et al. |
| 2009/0281380 | A1 | 11/2009 | Miller |

FOREIGN PATENT DOCUMENTS

| | | | |
|---|---|---|---|
| JP | S61-168357 A | | 7/1986 |
| JP | S63-34733 A | | 2/1988 |
| JP | 64-034048 A | | 2/1989 |
| JP | 02059170 A | * | 2/1990 |
| JP | H04-059344 A | | 2/1992 |
| JP | H06-007428 A | | 1/1994 |
| JP | H07-223763 A | | 8/1995 |
| JP | H07-330930 A | | 12/1995 |
| JP | 8-56895 A | | 3/1996 |
| JP | H08-071031 A | | 3/1996 |
| JP | H10-108909 A | | 4/1998 |
| JP | H11-019029 A | | 1/1999 |
| JP | 2000-025823 A | | 1/2000 |
| JP | 2000-79086 A | | 3/2000 |
| JP | 2000-279373 A | | 10/2000 |
| JP | 2000-300570 A | | 10/2000 |
| JP | 2001-091860 | | 4/2001 |
| JP | 2001-112740 A | | 4/2001 |
| JP | 2001-137182 A | | 5/2001 |
| JP | 2001-149313 A | | 6/2001 |
| JP | 2002-506369 A | | 2/2002 |
| JP | 2002-201297 A | | 7/2002 |
| JP | 2003-071937 A | | 3/2003 |
| JP | 3095748 U | | 5/2003 |
| JP | 2003-200540 A | | 7/2003 |
| JP | 2003-210394 A | | 7/2003 |
| JP | 2003-210395 A | | 7/2003 |
| JP | 2003-530135 A | | 10/2003 |
| JP | 2005-124961 A | | 5/2005 |
| WO | WO 98/58690 | | 12/1998 |
| WO | WO 00/59376 | | 10/2000 |
| WO | WO 2005/065526 | | 7/2005 |

OTHER PUBLICATIONS

Office Action issued by the Chinese Patent Office on Dec. 14, 2007 in connection with corresponding Chinese Patent Application No. 2005800021350.

1994-2007 China Academic Journal Electronic Publishing House. http://www.cnki.net (2nd ref in China Office Action issued Dec. 14, 2007 in connection with corresponding Chinese Application No. 2005800021350).

Supplementary European Search Report dated Apr. 14, 2009 in corresponding European Application No. EP 05 70 3382.

Japanese Office Action mailed Mar. 31, 2009 in corresponding Japanese Application No. 2004-002424 (with partial English language translation).

International Search Report PCT/JP2005/000116 dated Apr. 6, 2005.

* cited by examiner

MEDICAL CAPSULE HOUSING FORMED BY THERMAL WELDING

CROSS-REFERENCE TO RELATED APPLICATIONS

This application is a divisional of prior application Ser. No. 11/483,050, filed Jul. 7, 2006 by Toshimasa AKAGI, et. al. entitled MEDICAL CAPSULE HOUSING FORMED BY THERMAL WELDING which is a continuation of PCT international application Ser. No. PCT/JP2005/00116, filed Jan. 7, 2005 which designates the United States, incorporated herein by reference, and which claims the benefit of priority from JP-A No. 2004-002424 (KOKAI), filed Jan. 7, 2004, and JP-A NO. 2004-075066 (KOKAI), filed Mar. 16, 2004, both incorporated herein by reference.

BACKGROUND OF THE INVENTION

1. Field of the Invention

The present invention relates to a capsule-type medical apparatus such as a swallowing type capsule-type endoscope which is introduced into a test subject to collect information on inside of the test subject, particularly to a capsule-type medical apparatus which holds high liquid-tightness, a medical capsule housing which constitutes an exterior package of a medical capsule for performing observation, diagnostic examination or treatment in the test subject, and a production method thereof.

2. Description of the Related Art

In recent years, a capsule-type endoscope into which an imaging function and a wireless transmission function are incorporated emerges in the field of an endoscope. After a subject which is of the test subject swallows the capsule-type endoscope in order to perform the observation (diagnostic examination), the capsule-type endoscope passes through insides (body cavity) of the organs such as the stomach and the small intestine by vermicular movements of alimentary canals, and the capsule-type endoscope sequentially takes images with the imaging function during an observation period until the capsule-type endoscope is naturally discharged to the outside of the subject.

The capsule-type endoscope travels through inside the organs during the observation period, and picks up images of the inside of the body cavity as image data. The image data is sequentially transmitted to an external device provided outside the test subject by wireless transmission function such as a wireless communication, and stored in a memory in the external device. The subject carries the external device having the wireless transmission function and the memory function. The subject can move freely after swallowing the capsule-type endoscope until discharging the capsule-type endoscope, i.e., during the observation period. After the observation, a doctor or a nurse makes a diagnosis by displaying the images inside the body cavity on a display unit such as a monitor device based on the image data stored in a memory of an external device.

Some of the above-described capsule-type endoscopes are configured as swallowing-type capsule-type endoscopes, for example, as shown in JP-A No. 2001-91860 (KOKAI) in order to execute the above functions. The capsule-type endoscope proposed in JP-A No. 2001-91860 (KOKAI) includes function executing units inside. The function executing units are, for example, an illumination unit such as a light emitting diode (LED), a solid-state imaging device such as a charge coupled device (CCD) and a complementary metal oxide semiconductor (CMOS), a drive circuit for the illumination unit and the solid-state imaging device, a power supply unit including a battery, and a transmission unit which transmits image data from the solid-state imaging device to an external device. The function executing unit is accommodated in a sealed capsule-shape container. The capsule-shape container is formed while divided into a hemispherical transparent cover and a cylindrical outer casing. The hemispherical transparent cover serves to allow the illumination unit to illuminate the outside of the container, and receives the illumination light reflected from the outside to form an image of the outside of the container. The cylindrical outer casing accommodates the function executing unit. At the manufacture of the capsule-type endoscope, the transparent cover and the outer casing are bonded in a liquid-tight manner so that the capsule-shape container is sealed.

SUMMARY OF THE INVENTION

A capsule-type medical apparatus according to one aspect of the present invention includes a distal-end cover which is formed in a substantially hemispherical dome shape, the distal-end cover having an open bonding end portion; a drum portion cover which is formed in a hollow cylindrical shape, the drum portion cover having an open bonding end portion; a function executing unit which executes a predetermined preset function, the function executing unit being accommodated in the drum portion cover; and an electric storage unit which accumulates drive electric power for driving the function executing unit, wherein the bonding end portion of the distal-end cover and the bonding end portion of the drum portion cover are subjected to a surface treatment, the bonding end portion of the distal-end cover and the bonding end portion of the drum portion cover are bonded after the surface treatment to form an outer casing which has a capsule shape insertable into a test subject and which seals an inside in a liquid tight manner.

A medical capsule housing according to another aspect of the present invention includes a first outer member which is made of a resin material, the first outer member being formed in a cylindrical shape, the first outer member having an opening at one end portion, the opening being opened with a predetermined inner diameter; a second outer member which is made of a resin material, the second outer member being formed in a cylindrical shape, the second outer member having an opening at one end portion, the opening being opened with a diameter larger than an outer diameter of the opening of the first outer member; and a thermal welding portion in which fitting portions of the first outer member and the second outer member are fixed in close contact by thermal welding, the thermal welding acting on the fitting portion from an outside, the fitting portion being formed by inserting an outer circumferential surface side of the opening of the first outer member into an inner circumferential surface of the opening of the second outer member by a predetermined amount.

According to a medical capsule housing production method according to still another aspect of the present invention, an ultrasonic welding machine having a horn and a die performs ultrasonic welding of an opening end portion of a first outer member and an opening end portion of a second outer member, the medical capsule housing having a hollow hemispherical portions at end portions of the first outer member and the second outer member, one of the first and the second outer members has a step portion on an outer circumferential surface of the hollow hemispherical portion, the step portion serving to arrange the die, another of the first and the second outer members has a step portion on an outer circumferential surface of the hollow hemispherical portion, the step portion serving to arrange the horn.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a capsule-type medical apparatus according to the present invention will be described in detail with reference to FIGS. 1 to 13. The present invention is not limited to the embodiments, but various changes and modifications may be made without departing from the spirit and scope of the invention.

Figure 1:
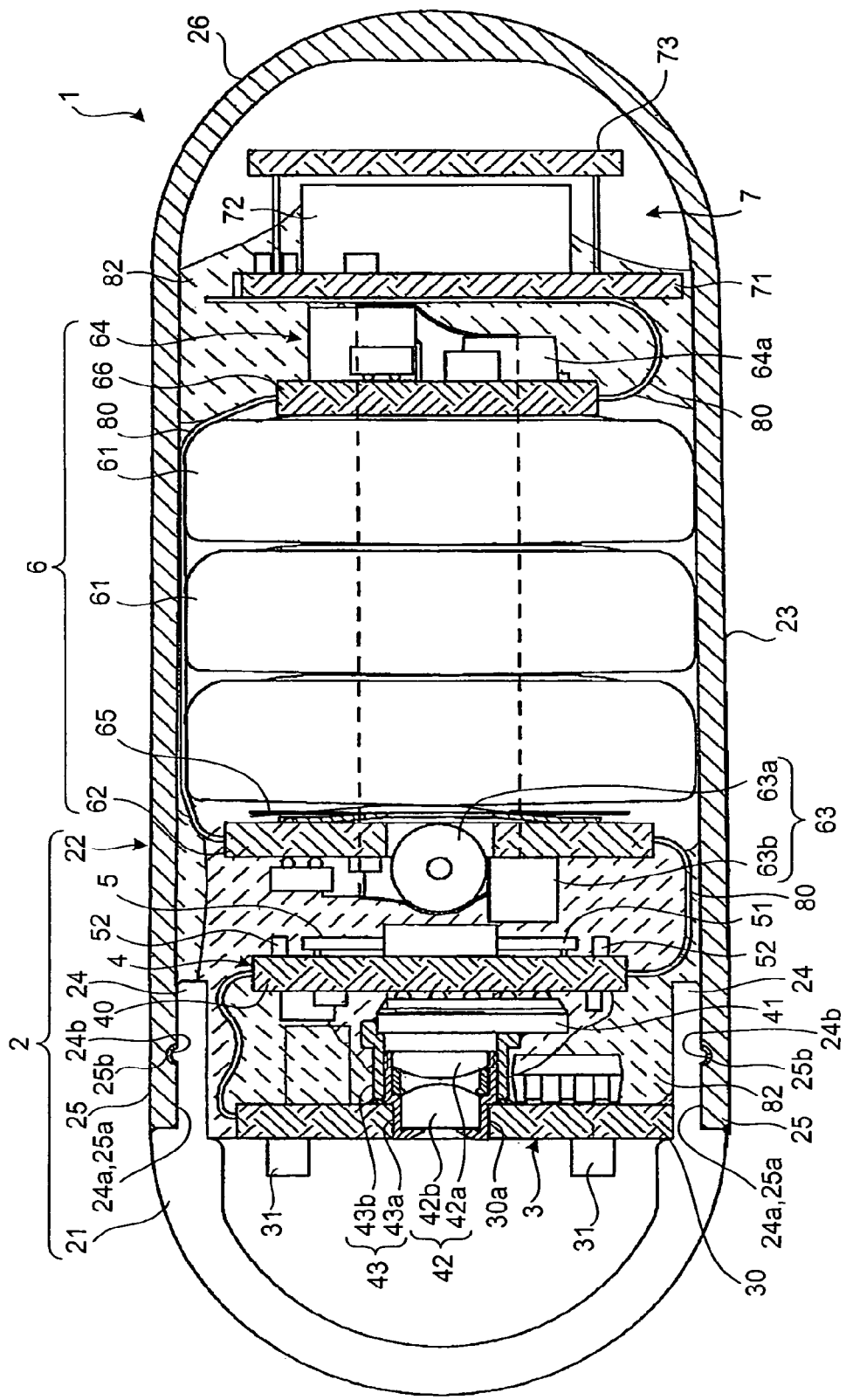
FIG. 1 is a sectional side view showing a configuration of a first embodiment of a capsule-type medical apparatus according to the present invention.
Figure 2:
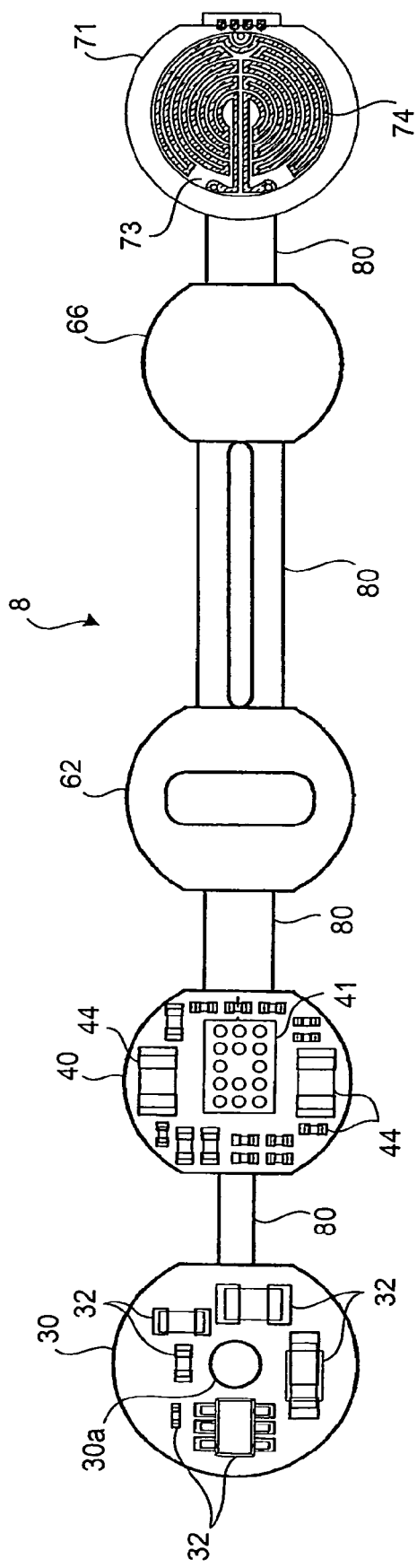
FIG. 2 is a top view showing un unfolded form of a rigid/flexible wiring board shown in FIG. 1.

FIG. 1 is a sectional side view showing a configuration of a first embodiment of a capsule-type medical apparatus according to the invention, and FIG. 2 is a top view showing an unfolded form of a rigid/flexible wiring board shown in FIG. 1. In the first embodiment, a capsule-type endoscope, which is introduced from the mouth of a human or the like which is of the test subject into the body cavity to take the images of test regions of the test subject, will be described as an example of the capsule-type endoscope.

As shown in FIG. 1, a capsule-type endoscope 1 includes a sealed container 2, an illumination unit 3, an imaging unit 4, a control unit 5, an electric storage unit 6, and a wireless transmission unit 7. The illumination unit 3 and the imaging unit 4 are function executing units that serve to execute preset predetermined functions. The sealed container 2 is an outer casing formed in the capsule shape. The illumination unit 3 emits the illumination light which illuminates the test region in the body cavity. The imaging unit 4 receives the reflected light of the illumination light, and takes the image of the test region. The control unit 5 performs drive control and signal processing of the illumination unit 3 and the imaging unit 4. The electric storage unit 6 accumulates drive electric power for driving the function executing unit. The wireless transmission unit 7 wirelessly transmits the image data obtained by the imaging unit 4 to the outside of the test subject.

A size of the sealed container 2 is such that a human can swallow the sealed container 2. The sealed container 2 is formed by elastically fitting a substantially hemispherical distal-end cover 21 and a cylindrical drum portion cover 22. The distal-end cover 21 is formed in a substantially hemispherical dome shape, and a rear side of the dome is opened. The distal-end cover 21 is molded by a transparent member having transparency or translucency such as cycloolefin polymer or polycarbonate that are preferable for securing optical performance and strength. The distal-end cover 21 enables the illumination light emitted from the illumination unit 3 to be transmitted to the outside of the sealed container 2, and the distal-end cover 21 enables the light reflected from the test subject to be transmitted to the inside of the sealed container 2.

The drum portion cover 22 is disposed at a rear side of the distal-end cover 21 and covers the function executing unit. In the drum portion cover 22 is configured of a cylindrical drum portion 23 and a substantially hemispherical dome-shape rear end portion 26. The drum portion 23 and the rear end portion 26 are integrally formed, and a front side of the drum portion 23 is opened in a circular shape. The drum portion cover 22 is made of a material such as polysulfone which is preferable for securing strength. The illumination unit 3, the imaging unit 4, and the control unit 5 are accommodated in the drum portion 23, and the wireless transmission unit 7 is accommodated in the rear end portion 26.

In the opening of the distal-end cover 21, a cylindrical bonding end portion 24 is provided along an edge of the opening end portion. In the opening of the drum portion 23, a cylindrical bonding end portion 25 is provided along an edge of the opening end portion. The bonding end portions 24 and 25 have bonding surfaces 24a and 25a respectively. The bonding surfaces 24a and 25a come into contact with each other while overlapping each other, when the distal-end cover 21 and the drum portion cover 22 are bonded to each other. In the first embodiment, the bonding end portion 24 of the distal-end cover 21 is located inside the sealed container 2, and the outer surface of the bonding end portion 24 constitutes the bonding surface 24a. The bonding end portion 25 of the drum portion cover 22 is located outside the sealed container 2, and the inner surface of the bonding end portion 25 constitutes the bonding surface 25a. An outer diameter of the bonding surface 24a is formed substantially equal to an inner diameter of the bonding surface 25a. In the bonding end portions 24 and 25, a draft angle is set straight at zero degree in molding. The bonding end portions 24 and 25 are formed in cylindrical shape, and the outer and inner diameters of the bonding end portions 24 and 25 are substantially the same. Therefore, the bonding end portions 24 and 25 are easily bonded to each other.

A projection 24b is formed in an endless manner over the circumference of the bonding surface 24a, and a groove 25b is formed in an endless manner over the circumference of the bonding surface 25a. The projection 24b and the groove 25b are bonded to each other while the bonding surfaces 24a and 25a overlap with each other. Thus, the projection 24b and the groove 25b are bonded to each other to constitute the bond maintaining unit for maintaining the state in which the distal-end cover 21 and the drum portion cover 22 are bonded.

As shown in FIG. 1, the illumination unit 3 includes an illumination board 30, four light emitters 31, and a chip component 32. The illumination board 30 is formed in a disc shape, and a through hole 30a is made in a central portion of the illumination board 30. The light emitter 31 is formed by a light emission diode such as a white light LED, and the light emitter 31 is provided in a front surface (on the side of the distal-end cover 21 in FIG. 1) of the illumination board 30. As shown in FIG. 2, the chip component 32 is provided in a back surface (on the side of the imaging board 40 in FIG. 1) of the illumination board 30, and the chip component 32 constitutes a circuit which drives the light emitter 31. The outside is illuminated with the illumination light emitted from the light emitter 31 through the distal-end cover 21.

As shown in FIG. 1, the imaging unit 4 includes an imaging board 40, a solid-state imaging device 41, and an imaging lens 42. The imaging board 40 is formed in the disc shape. The solid-state imaging device 41 such as the CCD and the CMOS is provided in the front surface (on the side of the illumination board 30 in FIG. 1) of the imaging board 40. The imaging lens 42 forms an image of a subject onto the solid-state imaging device 41. The imaging lens 42 is provided in the front surface (on the side of the illumination board 30 in FIG. 1) of the solid-state imaging device 41. The imaging lens 42 includes a first lens 42a and a second lens 42b. The first lens 42a is provided in a fixed frame 43a while located on the subject side, and the second lens 42b is provided in a movable frame 43b while located on the side of the solid-state imaging device 41. The fixed frame 43a and the movable frame 43b constitute a focus adjustment mechanism 43 which moves the second lens 42b along an optical axis. The fixed frame 43a is inserted into the through hole 30a of the illumination board 30, and the fixed frame 43a orientates the optical axis of the imaging lens 42 toward the front surface of the illumination board 30. Therefore, the imaging unit 4 can take the image in a range which is illuminated with the illumination light of the illumination unit 3. As shown in FIGS. 1 and 2, chip components 44 are provided in the front surface and the back surface (on the side of the switch board 62 in FIG. 1) of the imaging board 40 while surrounding the solid-state imaging device 41. The chip components 44 constitute a circuit which drives the solid-state imaging device 41.

As shown in FIG. 1, the control unit 5 has DSP (Digital Signal Processor) 51, and the DSP 51 is provided in the back surface of the imaging board 40 while surrounded by the chip component 52. The DSP 51 performs the drive control of the capsule-type endoscope 1, namely, the DSP 51 performs the drive control and output signal processing of the solid-state imaging device 41 and the drive control of the illumination unit 3. The chip components 44 located on the back surface of the imaging board 40 are a semiconductor member which has a function of mixing a video signal and a clock signal outputted from the DSP 51 into one signal when the signal is transmitted from the wireless transmission unit 7.

As shown in FIG. 1, the electric storage unit 6 includes a button-shaped dry battery 61, a switch board 62, a switch unit 63, and a power supply unit 64. For example, the button-shaped dry battery 61 is formed by a silver oxide battery. The switch board 62 is formed in the disc shape. The switch unit 63 includes a reed switch 63a and a bias magnet 63b, and the switch unit 63 is provided in the front surface (on the side of the imaging board 40 in FIG. 1) of the switch board 62. In the first embodiment, for example, the three button-shaped dry batteries 61 are arranged in series while a negative electrode cap is orientated toward the rear side. The battery is not limited to the silver oxide battery. For example, a rechargeable battery and a generating type battery may be used as the battery 61. The number of batteries is not limited to three.

A contact 65 formed by a plate spring is provided in the back surface of the switch board 62. The contact 65 comes into contact with a positive electrode can of the button-shaped dry battery 61, and the contact 65 biases the button-shaped dry battery 61 rearward (on the side of the power supply board 66 in FIG. 1) by biasing force of the plate spring.

The power supply unit 64 includes a power supply board 66 and a DC-DC converter 64a. The power supply board 66 is formed in the disc shape, and the DC-DC converter 64a is provided in the back surface (on the side of the rear end portion 26 in FIG. 1) of the power supply board 66. The DC-DC converter 64a performs boosting control, for example, of a voltage obtained by the button-shaped dry battery 61 in order to always supply the constant voltage to the system. A contact (not shown), which comes into contact with the negative electrode cap of the button-shaped dry battery 61, is provided in the front surface (on the side of the switch board 62 in FIG. 1) of the power supply board 66. In the first embodiment, in the electric storage unit 6, the button-shaped dry batteries 61 are arranged in series between the switch board 62 and the power supply board 66 to enable the electric power to be supplied to each of the function executing units.

The wireless transmission unit 7 includes a transmission board 71, an oscillation circuit 72, an antenna board 73, and an antenna 74. The transmission board 71 is formed in the disc shape. The oscillation circuit 72 is provided in the back surface (on the side of the rear end portion 26 in FIG. 1) of the transmission board 71. The antenna 74 is provided in the back surface (on the side of the rear end portion 26 in FIG. 1) of the antenna board 73. As shown in FIG. 2, the antenna 74 is formed in the back surface of the antenna board 73 with a substantially spiral pattern. In the wireless transmission unit 7, the oscillation circuit 72 takes out the signal having predetermined frequency, amplitude, and waveform from the signal to which the mixing is already performed by the chip component 44 (semiconductor member), and the taken-out signal is transmitted to the outside of the capsule-type endoscope 1 through the antenna 74. The transmission board 71 and the antenna board 73 are electrically connected by soldering to constitute the integral transmission unit.

The illumination board 30, the imaging board 40, the switch board 62, the power supply board 66, and the transmission board 71 are formed by a rigid board. As shown in FIG. 2, the rigid boards are provided while sandwiching each of a series of flexible boards 80, which constitutes a rigid and flexible wiring board 8. That is, the rigid boards are arranged at predetermined intervals through the flexible board 80 in the order of the illumination board 30, the imaging board 40, the switch board 62, the power supply board 66, and the transmission board 71. The rigid boards are electrically connected to one another. As shown in FIG. 1, the illumination board 30, the imaging board 40, the switch board 62, the power supply board 66, and the transmission board 71 are place one on another in a longitudinal direction from the side of the distal-end cover 21 to the side of the rear end portion 26 by folding the flexible board 80 of the rigid/flexible wiring board.

Generally, the rigid/flexible wiring board 8 is accommodated in the sealed container 2 while the flexible board 80 is folded. In the first embodiment, atmospheric plasma treatment is performed to the bonding end portions 24 and 25 to improve the bonding property as a pre-stage process. In the first embodiment, polysulfone used to form the drum portion cover 22 is not a material having the good adhesiveness to the adhesive agent. Therefore, in the first embodiment, the atmospheric plasma treatment is performed to the bonding surfaces 24a and 25a of the bonding end portions 24 and 25, and the atmospheric plasma treatment is also performed to the surface of the distal-end cover, which achieves the enhancement of the hydrophilicity.

Figure 3:
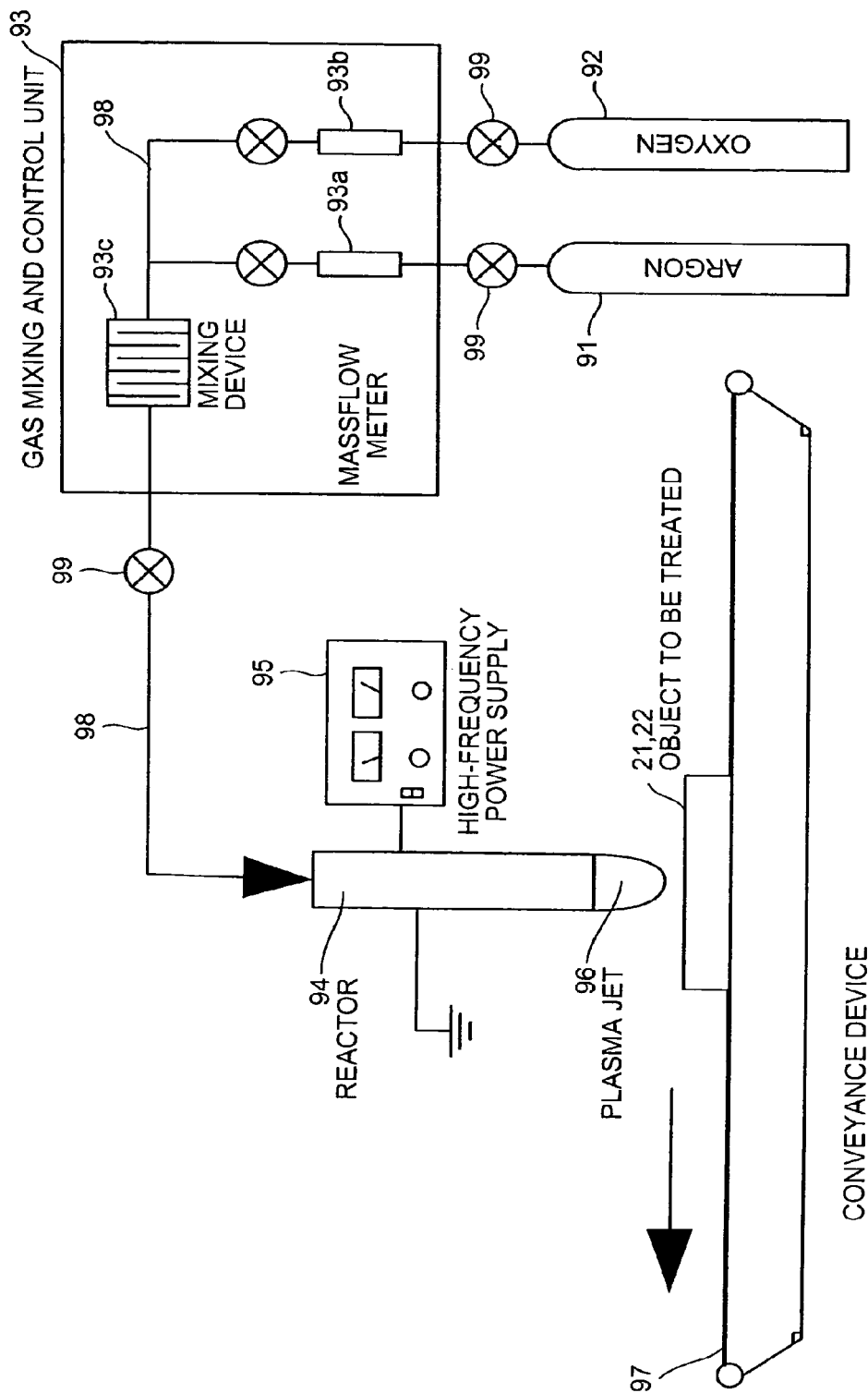
FIG. 3 is a view showing a configuration of a treatment apparatus which performs atmospheric plasma treatment.

FIG. 3 is a view showing a configuration of a treatment apparatus which performs the atmospheric plasma treatment. In FIG. 3, an atmospheric plasma treatment apparatus 90 includes gas bombs 91 and 92, a gas mixing and control unit 93, a plasma reactor 94, a high-frequency power supply 95, a plasma jet 96, a conveyance device 97, a gas transport path 98, and a valve 99. The gas bombs 91 and 92 are filled with argon gas and oxygen gas respectively. The gas mixing and control unit 93 mixes the argon gas and oxygen gas, and the gas mixing and control unit 93 controls the mixing of the gases and the amount of mixed gases. The plasma jet 96 performs plasma jet spray. The conveyance device 97 such as a conveyer conveys the distal-end cover 21 and the drum portion cover 22 which are of a substance to be treated. The valve 99 is provided on the gas transport path 98. In the atmospheric plasma treatment apparatus 90, massflow meters 93a and 93b in the gas mixing and control unit 93 adjust mixing flow rates of the argon gas and the oxygen gas, and a mixing device 93c mixes the adjusted amounts of argon gas and oxygen gas to send the mixed gas to the reactor 94.

Figure 4:
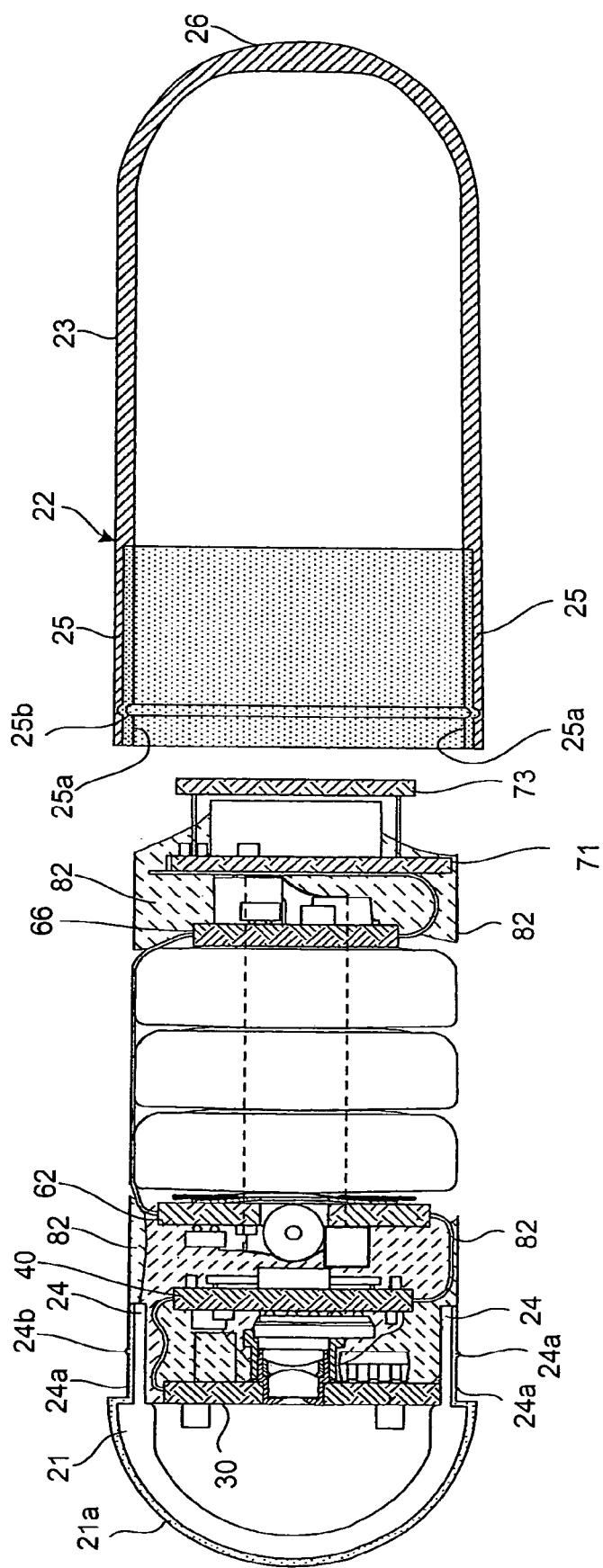
FIG. 4 is a view showing a state in which the capsule-type medical apparatus shown in FIG. 1 is assembled.

In the reactor 94, the mixed gas is ionized to generate the plasma by high-frequency voltage from the high-frequency power supply 95. The generated plasma becomes a jet stream, and the jet stream is sprayed from the plasma jet 96 to the outer surface 21a of the distal-end cover 21 and the bonding surfaces 24a and 25a of the distal-end cover 21 and drum portion cover 22 which are conveyed by the conveyance device 97. This enables the surface treatment as shown in FIG. 4. At this point, the distal-end cover 21 is placed on the conveyance device 97 while the outer surface is orientated upward, and the drum portion cover 22 is placed on the conveyance device 97 while the opening is orientated upward. The portion to which the plasma treatment is performed includes the projection 24b and the groove 25b.

In the outer surface 21a of the distal-end cover 21 and the bonding surfaces 24a and 25a of the distal-end cover 21 and the drum portion cover 22, many micro irregularities are formed to increase a surface area of the bonding surface. Therefore, the hydrophilicity is improved in the outer surface 21a of the distal-end cover 21, and the bonding surfaces 24a and 25a of the distal-end cover 21 and drum portion cover 22 come to adhere more tightly by the adhesive agent.

In the first embodiment, when the distal-end cover 21 and drum portion cover 22 in which the plasma treatment is completed are bonded to each other, the rigid/flexible wiring board 8 is attached to the distal-end cover 21 while the gap among the illumination board 30, the imaging board 40, and the switch board 62 and gaps among the power supply board 66, the transmission board 71, and the antenna board 73 are filled with a sealing resin 82. Then, the distal-end cover 21 is placed on a support base (not shown) such that the outer surface of the distal-end cover 21 is covered with the support base. The sealing resin 82 is applied to the outer surfaces of the structures constituting the function executing unit except for the antenna board 73 in order to fill the gaps between the outer surfaces and the inner surface of the sealed container 2 with the sealing resin 82. The adhesive agent is applied to the bonding surface 24a of the bonding end portion 24 of the distal-end cover 21. Then, the bonding end portion 25 of the drum portion cover 22 and the bonding end portion 24 of the distal-end cover 21 are bonded to each other while the bonding end portion 25 overlaps to the bonding end portion 24, and the projection 24b and groove 25b which are of the bond maintaining unit are engaged with each other. Therefore, the adhesive agent intrudes into the gap between the bonding surfaces 24a and 25a in which the adhesiveness is improved. Finally, the bonding surfaces 24a and 25a are relatively rotated while the projection 24b and the groove 25b are engaged with each other. Therefore, the adhesive agent intruding into the gap between the bonding surfaces 24a and 25a reaches the projection 24b and groove 25b, so that the distal-end cover 21 and the drum portion cover 22 are bonded to each other while the liquid-tightness is secured.

Thus, in the first embodiment, the many micro irregularities are formed in the surfaces to enhance the hydrophilicity by performing the plasma surface treatment to the outer surface of the distal-end cover and the bonding surfaces of the distal-end cover and drum portion cover. The distal-end cover and drum portion cover constitute the sealed container. Therefore, outside moisture (for example, moisture content inside the test subject) adheres evenly to the outer surface to improve the translucency of the distal-end cover, so that an observation view field in front of the distal-end cover can be enlarged, and the imaging unit can obtain the good observation image.

In the first embodiment, the surface area is increased by the many micro irregularities formed in the bonding surfaces of the distal-end cover and drum portion cover, and the large amount of adhesive agent adheres evenly to the bonding surface to improve the adhesiveness. Therefore, the bonded portions are hardly separated at the interface, and the outer casing can seal the inside in a liquid-tight manner. Thus, the liquid-tightness of the container can be secured to further enhance the safety.

In the first embodiment, the projection and the groove are provided in the bonding surface, and the bonding state between the distal-end cover and the drum portion cover is maintained during the assembly by engaging the projection and the groove with each other, so that the safety can be further enhanced while the liquid-tightness of the container is secured.

In the first embodiment, the plasma treatment is performed as the surface treatment of the cover. The invention is not limited to the plasma treatment. For example, the surface treatment of the cover can also be performed using an active gas other than the plasma such as ozone and an ultraviolet ray. The hydrophilicity of the outer surface or bonding surface of the cover, which is of the portion to be treated, can also be improved by chemical treating with chemicals or primer treating.

Figure 5:
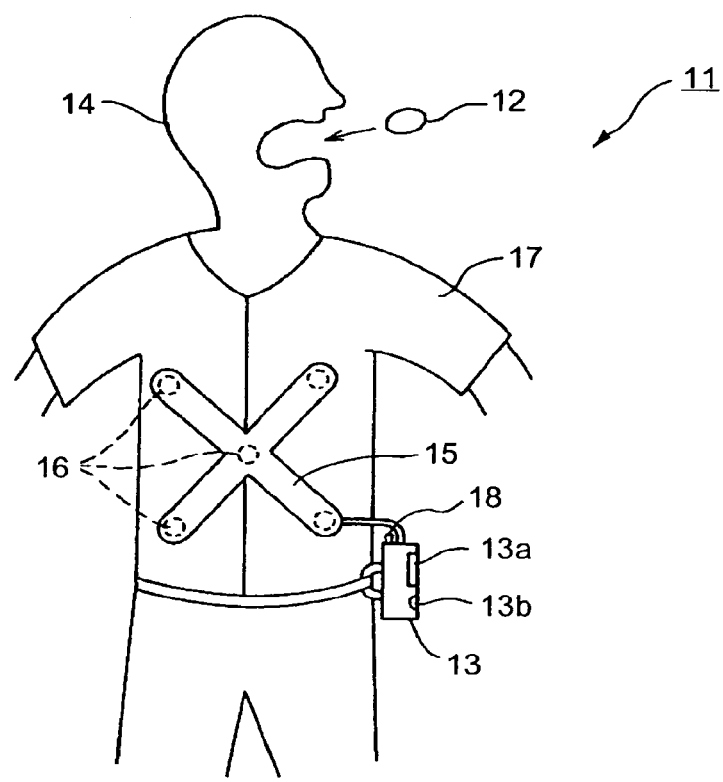
FIG. 5 is a view for explaining a capsule-type endoscope and an external device which constitute an in-vivo information acquiring system.
Figure 6:
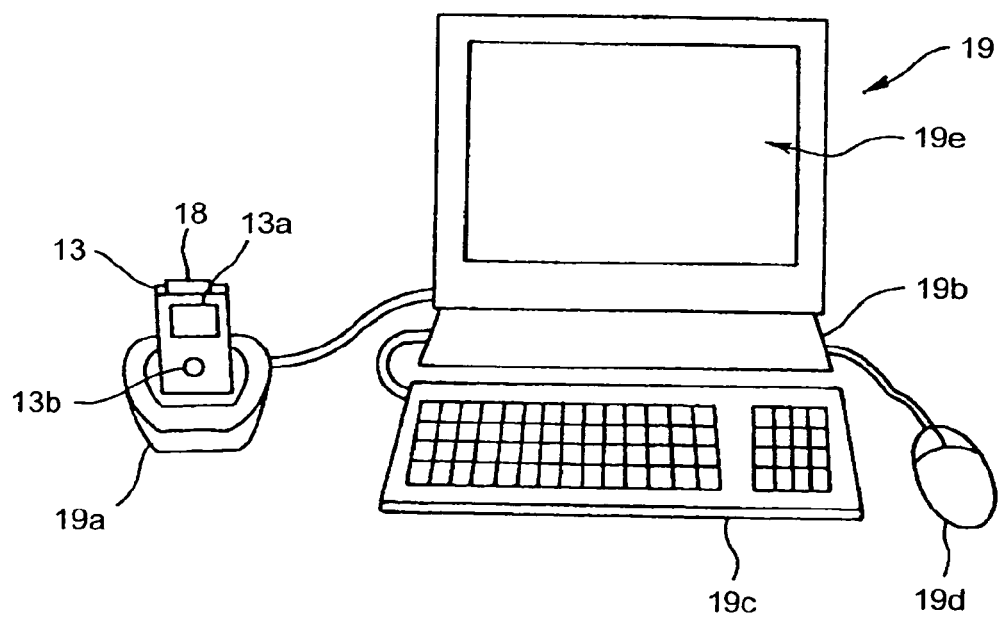
FIG. 6 is a view for explaining the external device and a terminal device which constitute the in-vivo information acquiring system.
Figure 7:
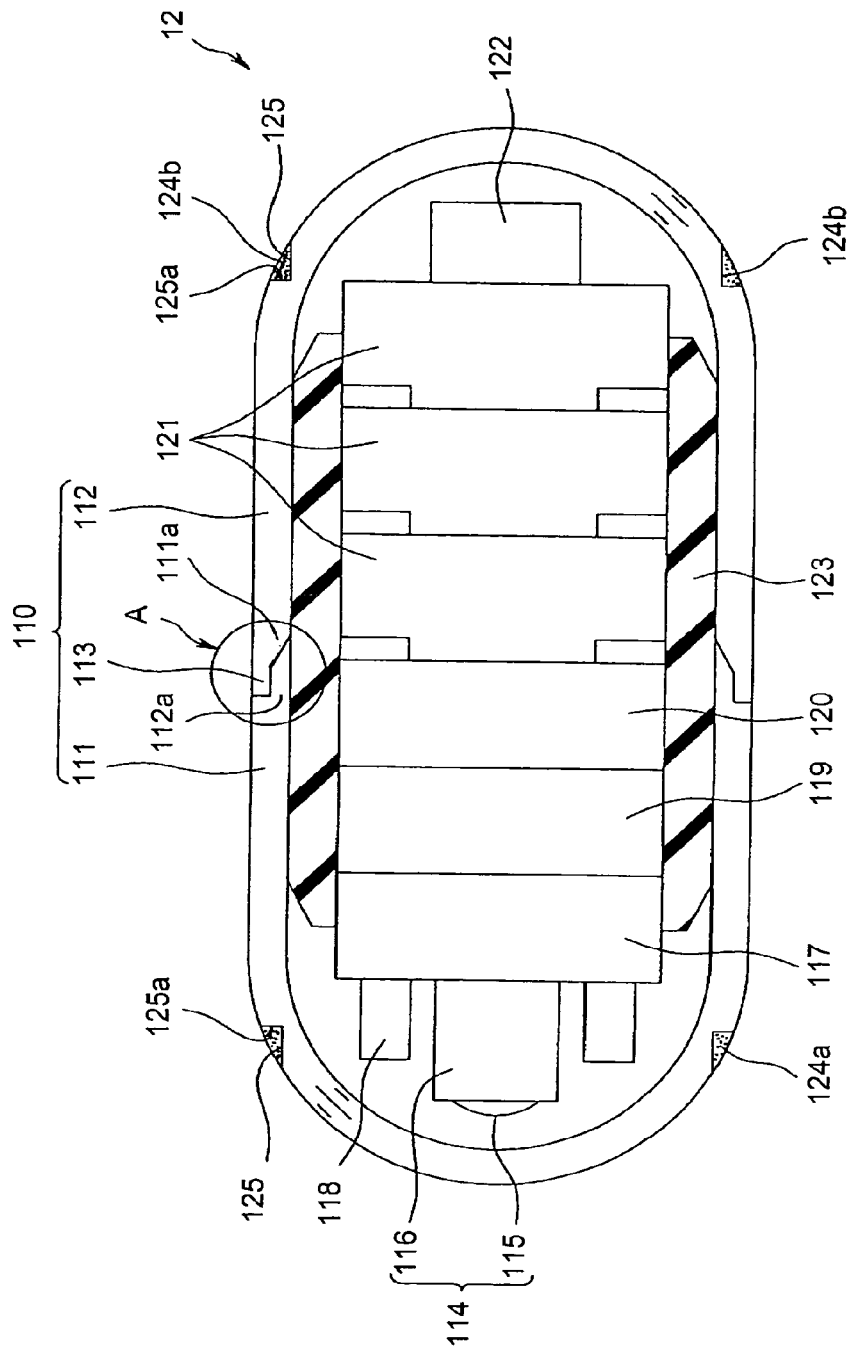
FIG. 7 is a sectional side view showing a configuration of a second embodiment of the capsule-type medical apparatus according to the present invention.
Figure 8:
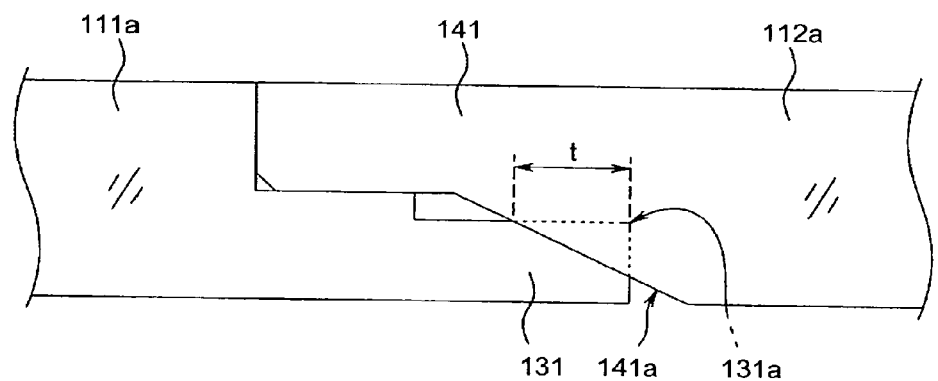
FIG. 8 is a view for explaining configuration of openings of an observation-side cover and a capsule main body, which constitute an A portion shown in FIG. 7.
Figure 9:
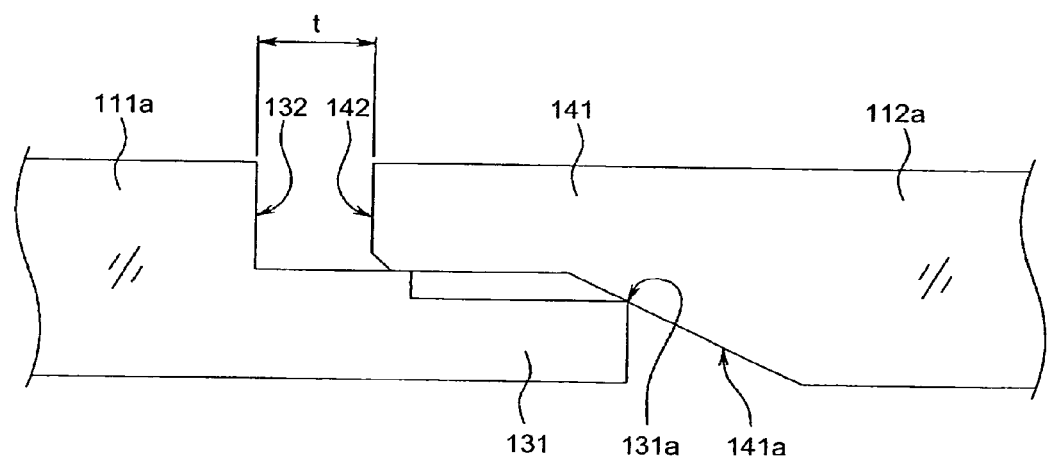
FIG. 9 is a view for explaining a positional relationship between the observation-side cover and the capsule main body when the A portion shown in FIG. 7 is formed.
Figure 10:
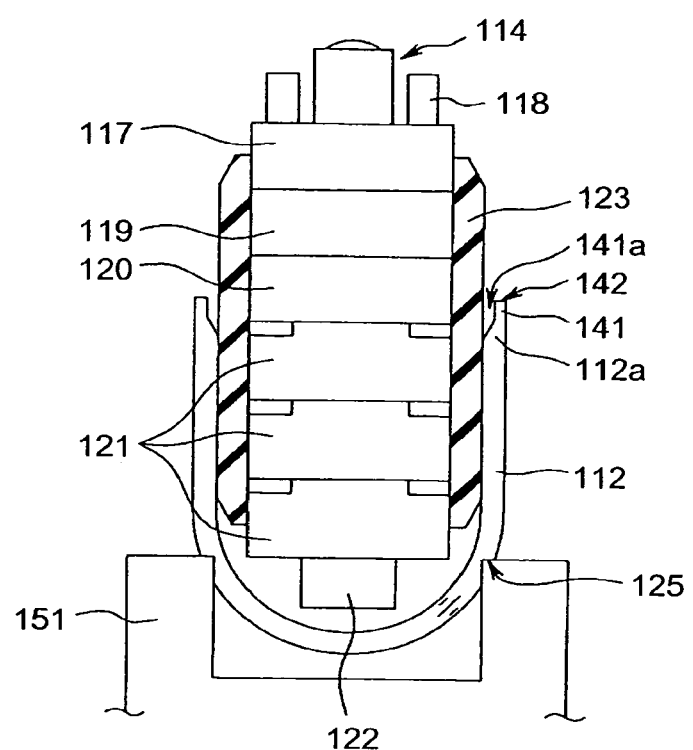
FIG. 10 is a view showing a state in which the capsule main body is arranged in a die.
Figure 11:
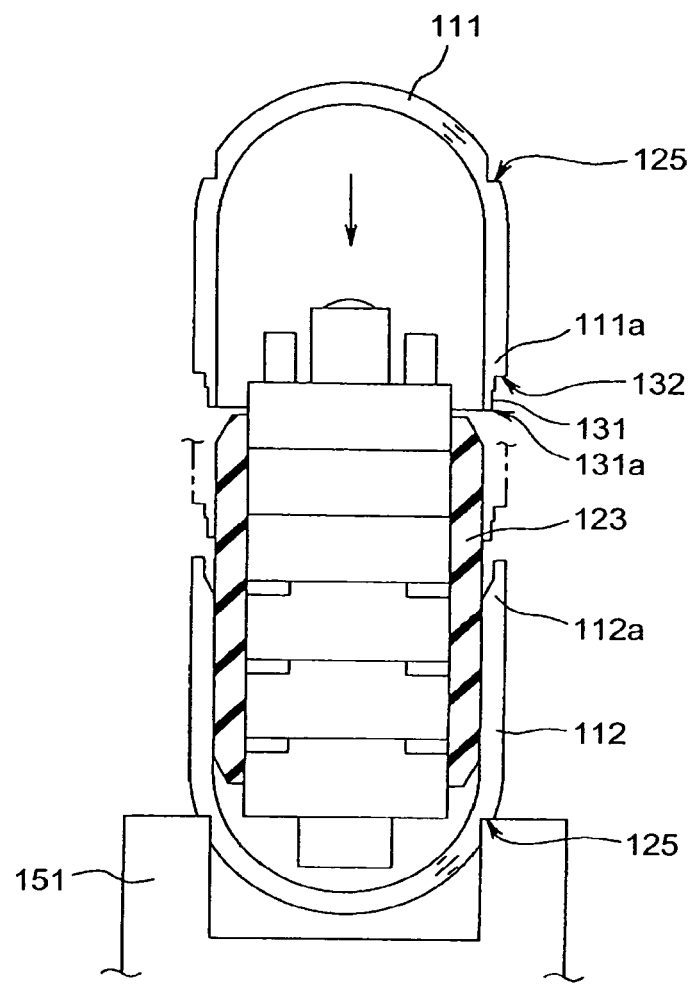
FIG. 11 is a view showing a state in which the capsule main body arranged in the die is arranged in the observation-side cover.
Figure 12:
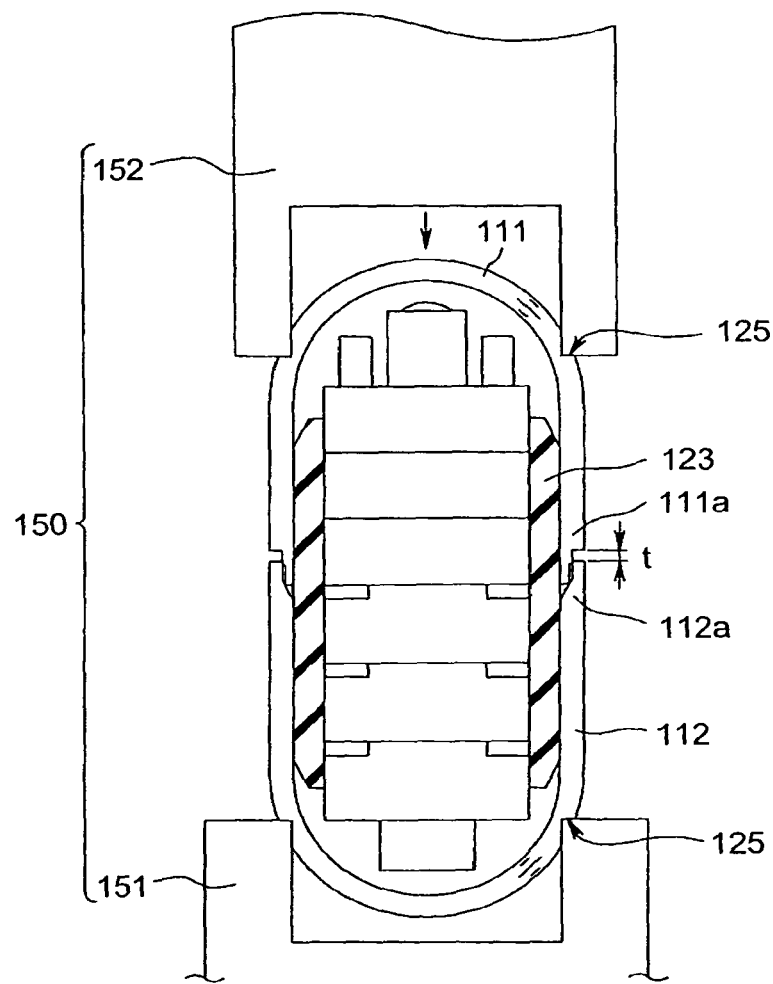
FIG. 12 is a view for explaining an ultrasonic welding starting state in which a horn is arranged in the observation-side cover to start ultrasonic welding.

FIGS. 5 to 12 show a second embodiment of the invention. FIG. 5 is a view for explaining a capsule-type endoscope and an external device which constitute the capsule-type endoscope (hereinafter referred to as "in-vivo information acquiring system"), FIG. 6 is a view for explaining the external device and a terminal device which constitute the in-vivo information acquiring system, FIG. 7 is a sectional side view showing a configuration of the second embodiment of the capsule-type medical apparatus, FIG. 8 is a view for explaining a configuration of openings of an observation-side cover and a capsule main body which constitute an A portion shown in FIG. 7, FIG. 9 is a view for explaining a positional relationship between the observation-side cover and the capsule main body when the A portion shown in FIG. 7 is formed, FIG. 10 is a view showing a state in which the capsule main body is arranged in a die, FIG. 11 is a view showing a state in which the capsule main body arranged in the die is arranged in the observation-side cover, and FIG. 12 is a view for explaining an ultrasonic welding starting state in which a horn is arranged in the observation-side cover to start ultrasonic welding. In the second embodiment, a medical capsule is described as the capsule-type endoscope.

As shown in FIGS. 5 and 6, an in-vivo information acquiring system 11 mainly includes a capsule-type endoscope 12 and an external device 13. The capsule-type endoscope 12 is a capsule-type medical apparatus according to the invention. For example, when a test subject (hereinafter occasionally referred to as "subject") 14 swallows the capsule-type endoscope 12, the capsule-type endoscope 12 is introduced into the body cavity. The capsule-type endoscope 12 introduced into the body cavity of the test subject obtains test subject information such as image information of the body cavity. The test subject information obtained by the capsule-type endoscope 12 is wirelessly transmitted to the external device 13.

The external device 13 is arranged outside the subject 14. For example, the external device 13 is formed in a box shape, and a liquid crystal monitor 13a and an operation unit 13b are provided in the front surface of the box portion. The liquid crystal monitor 13a displays the image, and an operator provides an operation instruction through the operation unit 13b. The external device 13 is also provided with an antenna unit 15 which receives the test subject information wirelessly transmitted from the capsule-type endoscope 12. The antenna unit 15 includes plural antennas 16, 16, . . . . The antenna unit 15 is provided, for example, in a jacket 17 which the subject 14 wears.

A recording medium 18 such as CompactFlash (registered trademark) memory which is of the portable test subject information recording unit is attached to the external device 13 during the diagnostic examination of the body cavity with the capsule-type endoscope 12. The test subject information is transmitted from the capsule-type endoscope 12 and received by the external device 13, and the test subject information is stored in the recording medium 18. Then, the test subject information is captured by a terminal device 19 such as a personal computer or the like.

The shape of the antenna unit 15 is not limited to the shape shown in FIG. 5. In the second embodiment, the antenna unit 15 is provided in the jacket 17 which the subject 14 wears. However, instead of providing the antenna unit 15 in the jacket 17, the antenna unit 15 may be directly bonded to the body surface of the subject 14. For example, the external device 13 is detachably attached to a belt which the subject wears with a hook. A remaining battery power level warning display LED which indicating that a remaining battery level is low may be provided in the external device 13, or the external device 13 may be configured such that only the power switch is provided but no operation unit 13b.

As shown in FIG. 6, the external device 13 is attached to a cradle 19a which is also used as a battery charger, or the external device 13 is electrically connected to the terminal device 19 through a USB cable (not shown) or the like. The test subject information such as the image stored in the external device 13 is retrieved into a terminal main body 19b of the terminal device 19. An input and operation device such as a keyboard 19c and a mouse 19d is operated in the retrieval work of the image. The image retrieved into the terminal device 19 can be displayed on a monitor unit 19e by operating the keyboard 19c or a mouse 19d.

As shown in FIG. 7, in the capsule-type endoscope 12 of the second embodiment, an observation optical unit, an illumination unit, a peripheral circuit components, and a power supply unit are arranged inside a medical capsule housing (hereinafter abbreviated as capsule) 110 as described later.

The capsule 110 includes an observation-side cover 111 which is of the first outer member and a capsule main body 112 which is of the second outer member. The observation-side cover 111 and the capsule main body 112 are formed in a cylindrical shape in which an opening is provided on one end portion side while the other end portion is formed in, e.g., a hollow hemispherical portion. A cover-side opening end portion 111a of the observation-side cover 111 and a main body-side opening end portion 112a of the capsule main body 112 are closely fixed to each other in a watertight manner at boundary surface by a thermal welding portion 113.

In the second embodiment, the observation-side cover 111 and the capsule main body 112 are made of clear and colorless polycarbonate. The polycarbonate is a thermoplastic resin having both a given transparency and biocompatibility.

An objective optical system 114 is provided at a predetermined position inside the hollow hemispherical portion of the observation-side cover 111. The objective optical system 114 forms the optical image incident through the observation-side cover 111. The objective optical system 114 includes an objective lens 115 and an optical lens (not shown) arranged in a lens frame 116. An imaging device such as a CCD imager 117 is arranged at an imaging position of the objective optical system 114. Plural (for example, four) white light LEDs 118, which is of an illumination optical system, are arranged in the same plane around the objective optical system 114.

A signal processing circuit 119, a communication processing circuit 120, and plural batteries 121 such as button-shaped batteries for supplying the electric power are arranged in the back surface of the CCD imager 117. The signal processing circuit 119 includes a circuit which drives light emission of the white light LED 118, a circuit which drives the CCD imager 117, and a circuit which performs a process of converting the imaging signal outputted from the CCD imager 117 into the image signal. The communication processing circuit 120 performs a process of transmitting the image signal generated by the signal processing circuit 119 to the external device 13 in the form of a radio wave. An antenna 122 is arranged on the rear end side of the button-shaped battery 121, namely, inside the hollow hemispherical portion of the capsule main body 112. The communication processing circuit 120 is electrically connected to the antenna 122. Therefore, the signal processed by the communication processing circuit 120 is transmitted to the external device 13 through the antenna 122.

In the second embodiment, a tubular member 123 is arranged in the capsule 110. The CCD imager 117, the signal processing circuit 119, the communication processing circuit 120, and the button-shaped battery 121 are arranged in the tubular member 123. The numerals 124a and 124b designate a later-mentioned filled portion.

The configuration of the boundary surface which becomes the thermal welding portion including the opening end portion of the observation-side cover 111 and the opening end portion of the capsule main body 112 will specifically be described with reference to FIGS. 8 and 9.

As shown in FIG. 8, an inner circumferential surface-side projection 131 constituting a cover-side opening which is opened with a predetermined inner diameter is opened in the cover-side opening end portion 111a constituting the opening end portion of the observation-side cover 111. An edge-line portion 131a formed with a sharp edge is arranged over the circumference in the distal-end portion of the inner circumferential surface-side projection 131.

On the other hand, an outer circumferential surface-side projection 141 constituting a main body-side opening is formed in the main body-side opening end portion 112a constituting the opening end portion of the capsule main body 112. The diameter of the main body-side opening formed by the outer circumferential surface-side projection 141 is larger than the outer diameter of the inner circumferential surface-side projection 131 constituting the cover-side opening by a predetermined size. That is, the outer circumferential surface-side projection 141 of the capsule main body 112 is arranged to be fitted over the inner circumferential surface-side projection 131 of the observation-side cover 111.

The inner circumferential surfaces of the outer circumferential surface-side projection 141 and capsule main body 112 are continuously formed by an inclined-surface portion 141a. A relationship between the inclined-surface portion 141a and the edge-line portion 131a is configured such that the edge-line portion 131a interferes by a predetermined amount t as shown by a broken line when the observation-side cover 111 and the capsule main body 112 are arranged while brought into close contact with each other. That is, the edge-line portion 131a and the inclined-surface portion 141a abut against each other when the capsule main body 112 is fitted over the observation-side cover 111.

That is, as shown in FIG. 9, when the capsule main body 112 is fitted over the observation-side cover 111 in order to form the capsule 110, the abutting portion which is formed by the contact between the edge-line portion 131a and the inclined-surface portion 141a comes to be located at the side of a closed space formed at the inner circumferential surface side of the capsule 110.

In the abutting state, a gap t which corresponds to an amount of an interference portion is formed between the cover outer circumference-side cover end face 132 of the observation-side cover 111 and a main body-side opening end surface 142 which is of the distal-end portion of the capsule main body 112. The interference portion becomes a melted portion in a later-mentioned ultrasonic welding process.

Step portions (designated by the numeral 125 in FIG. 7) are formed in the outer circumferential surfaces of the observation-side cover 111 and capsule main body 112 respectively. The horn and die, which constitute a later-mentioned ultrasonic welding machine, are arranged in the step portions 125 in ultrasonic welding respectively. The positions where the step portions 125 are formed in the observation-side cover 111 and capsule main body 112 are located on the outer circumferences of the hemispheres. An annular plane portion 125a is formed in the step portion 125. The annular plane portion 125a is perpendicular to an axis line connecting the center of the hollow hemispherical portion of the observation-side cover 111 and the center of the hollow hemispherical portion of the capsule main body 112.

The ultrasonic welding process of bonding the observation-side cover 111 and the capsule main body 112 will be described below. The tubular member 123 is assembled inside the capsule main body 112. The CCD imager 117, the signal processing circuit 119, the communication processing circuit 120, the button-shaped battery 121, and the antenna 122 are previously arranged in the tubular member 123 in a process prior to the ultrasonic welding process.

As shown in FIG. 10, the capsule main body 112 in which the tubular member 123 and the like are assembled is arranged in a die 151 constituting the ultrasonic welding machine. At this point, the step portion 125 formed in the capsule main body 112 is arranged at a predetermined position of the die 151, which allows the capsule main body 112 to be placed on the die 151.

As shown in FIG. 11, the observation-side cover 111 is arranged while oppositely facing the capsule main body 112 placed on the die 151. Then, the observation-side cover 111 is moved toward the side of the capsule main body 112 as shown by an arrow of FIG. 11, and the outer circumferential surface of the inner circumferential surface-side projection 131 is fitted into the inner circumferential surface of the outer circumferential surface-side projection 141 as shown by an alternate long and short dash line. Then, as shown in FIG. 9, the edge-line portion 131a of the observation-side cover 111 is caused to abut against the inclined-surface portion 141a of the capsule main body 112. This enables the predetermined gap t to be formed between the cover outer circumference-side cover end face 132 and the main body-side opening end surface 142.

As shown in FIG. 12, a horn 152 constituting the ultrasonic welding machine 150 is caused to abut against the step portion 125 formed in the observation-side cover 111. Thus, pre-process setting is completed. Then, the ultrasonic welding is started with the ultrasonic welding machine 150. While fine ultrasonic vibrations are imparted from the horn 152 to the observation-side cover 111, pressing force shown by the arrow of FIG. 12 is imparted to the observation-side cover 111.

When the ultrasonic vibrations are imparted to the observation-side cover 111, the portion where the inclined-surface portion 141a and the edge-line portion 131a abut against each other is vibrated to produce friction, which allows the portion to be ultrasonically heated to start the melting.

The edge-line portion 131a is melted by the amount of interference portion by imparting the pressing force in the arrow direction, and the cover outer circumference-side cover end face 132 and the main body-side opening end surface 142 abut against each other at the boundary surface, which allows the boundary surface to be melted by the ultrasonic heating. Then, the ultrasonic vibration is stopped and the melted portion is cooled. Therefore, the portion melted by the ultrasonic heating is solidified to form the capsule 110 having the thermal welding portion 113 shown in FIG. 7 at which the observation-side cover 111 and the capsule main body 112 are integrally welded and fixed in the watertight manner.

The horn 152 is detached from the step portion 125 of the observation-side cover 111, and the capsule 110 in which the observation-side cover 111 and the capsule 112 are integrated with each other is taken out from the die 151. The capsule 110 is placed in a storage box or the like. Then, the new capsule main body 112 in which the tubular member 123 and the like are assembled is arranged on the die 151 of the ultrasonic welding machine 150 to perform the next welding work.

The step portions 125, which are formed in the observation-side cover 111 and capsule main body 112 of the welded capsule 110 stored in the storage box, are filled with the adhesive agents to provide adhesive agent filled portions 124a and 124b. Therefore, the capsule-type endoscope 12 shown in FIG. 7 is formed.

In the configuration of the second embodiment, the inner circumferential surface-side projection 131 is provided in the observation-side cover 111, and the outer circumferential surface-side projection 141 is provided in the capsule main body 112. Alternatively, the configuration in which the outer circumferential surface-side projection is provided in the observation-side cover 111 while the inner circumferential surface-side projection is provided in the capsule main body 112 may be adopted.

The capsule main body 112 may be arranged in the die after the observation-side cover 111 is previously fitted in the capsule main body 112.

Thus, the observation-side cover and the capsule main body are bonded by the ultrasonic welding with the ultrasonic welding machine, which allows the observation-side cover and the capsule main body to be integrally fixed in the watertight manner while the welding portion is provided only at the boundary surface between the observation-side cover and the capsule main body. Therefore, because the welding portion is formed only in the boundary surface, the post-processing is not required, and the watertight structure is obtained with little variation by simple process management.

Because the observation-side cover and the capsule main body are formed by the same resin member, a thermal welding defect caused by the variation in member can be prevented to obtain the secure thermal welding effect.

While the edge-line portion is provided at the distal-end of the inner circumferential surface-side projection of the observation-side cover, the inclined-surface portion continuously coupling the outer circumferential surface-side projection of the capsule main body and the inner circumferential surface of the capsule main body is formed such that the edge-line portion interferes by the predetermined amount. Therefore, in the ultrasonic heating generated by the ultrasonic vibration, the melting is started from the capsule inner circumferential side on which the edge-line portion and the inclined-surface portion abut against each other, and the watertightness in the capsule can be secured. In addition, the welding and fixing are performed even to the distal-end surface of the outer circumferential surface-side projection, so that the bonding property can be largely improved by the welding while the improvement of watertightness can further be achieved.

The step portions having the annular plane portions orthogonal to the axis line are provided at predetermined positions on the hemispherical outer circumferences of the observation-side cover and capsule main body. Therefore, in the state in which the die or horn constituting the ultrasonic welding machine are arranged in the step portions respectively, the pressing force can evenly be imparted to the boundary surface between the observation-side cover and the capsule main body to perform the ultrasonic welding, the portion where the die and horn constituting the ultrasonic welding machine abut against each other can be restricted to prevent accidental damage of the surface of the observation-side cover and capsule main body.

In the second embodiment, the capsule-type endoscope which obtains the test subject information such as the image information is described as an example of the medical capsule. However, the medical capsule is not limited to the capsule-type endoscope, but invention may be applied to a medical capsule into which the ultrasonic vibrator is incorporated and a medical capsule into which various sensors such as a temperature sensor, a pressure sensor, and a pH sensor are incorporated.

Figure 13:
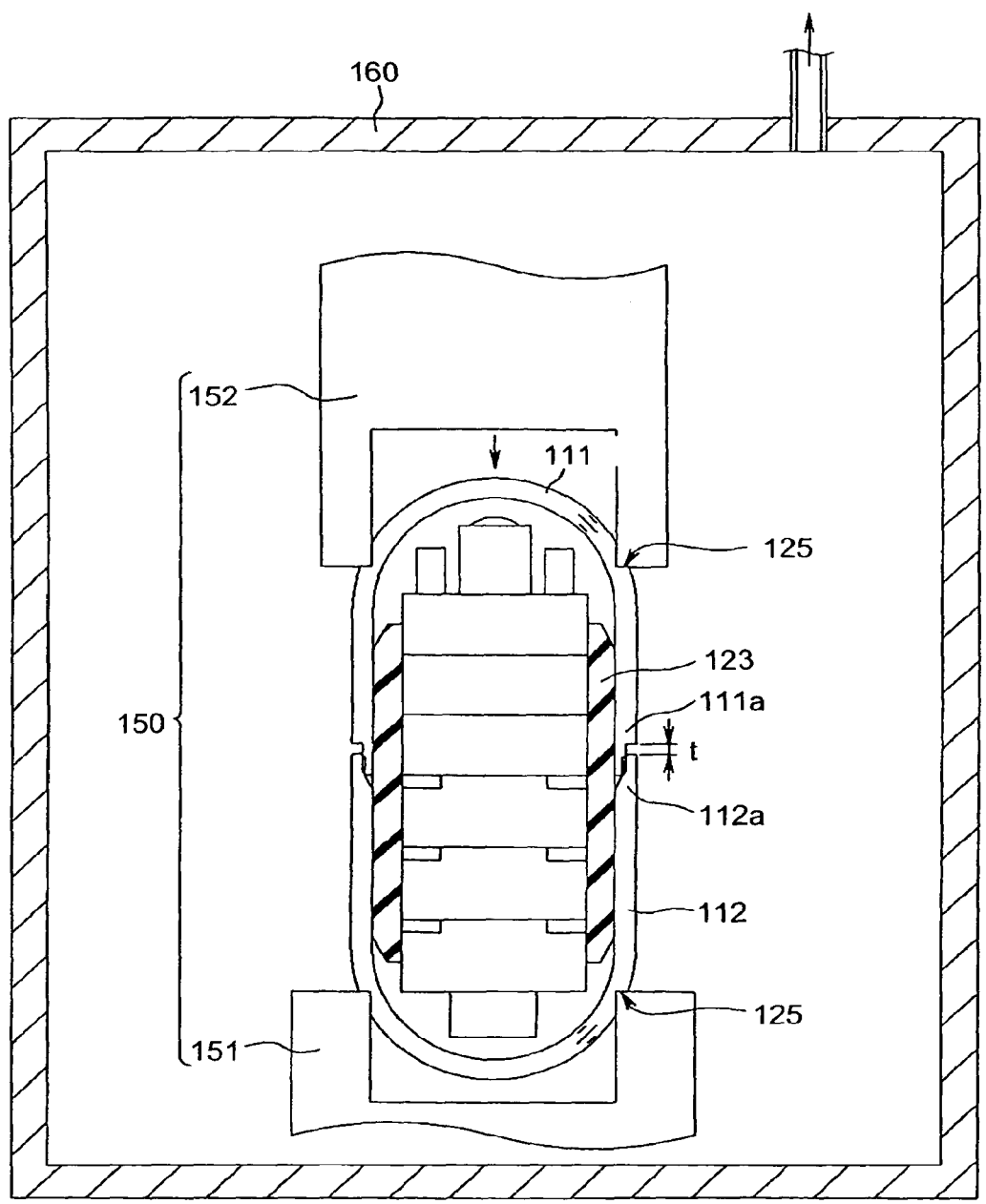
FIG. 13 is a view for explaining an example of ultrasonic welding work according to a third embodiment of the present invention.

FIG. 13 is a view for explaining an example of the ultrasonic welding work according to a third embodiment of the invention. As shown in FIG. 13, in the third embodiment, the ultrasonic welding machine 150 is arranged in a vacuum furnace 160, and the ultrasonic welding work is performed in a vacuum environment.

That is, in the third embodiment, as shown in FIG. 12, the capsule main body 112 in which the tubular member 123 and the like are assembled is arranged on the die 151 of the ultrasonic welding machine 150, the observation-side cover 111 is arranged in a predetermined state with respect to the capsule main body 112, and the horn 152 abuts against the step portion 125 of the observation-side cover 111. The vacuuming is performed at the setting completion time, and then the welding work is performed.

Therefore, air does not remain in the capsule inside space formed by the observation-side cover 111 and the capsule main body 112, so that air expansion caused by the volume change is not occurred in the period from the start of the welding work to the completion of the welding work.

Accordingly, in the ultrasonic welding, reaction force is prevented from acting in a direction in which the welding portion can be separated, and the welding state can securely be maintained.

The invention is not limited to the above embodiments, but various modifications may be made without departing from the spirit and scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of producing a medical capsule housing including a first outer member and a second outer member, the method comprising:
   arranging a die of an ultrasonic welding machine at a step portion that is on an outer circumferential surface of a hollow hemispherical portion of one of the first and the second outer members,
   arranging a horn of the ultrasonic welding machine at a step portion that is on an outer circumferential surface of a hollow hemispherical portion of another of the first and the second outer members; and
   performing ultrasonic welding of the opening end portions of the first and second outer members by using the ultrasonic welding machine.

2. The method according to claim 1, wherein the step portion provided in one of the outer members and the step portion provided in another outer member are formed in the same shape, and the step portions have annular plane portions, the annular plane portion being perpendicular to an axis line connecting centers of the hollow hemispherical portions.

3. The method according to claim 1, further comprising:
   arranging the ultrasonic welding machine in a vacuum furnace.

* * * * *

UNITED STATES PATENT AND TRADEMARK OFFICE
CERTIFICATE OF CORRECTION

PATENT NO. : 8,709,329 B2  Page 1 of 1
APPLICATION NO. : 13/080999
DATED : April 29, 2014
INVENTOR(S) : Akagi et al.

It is certified that error appears in the above-identified patent and that said Letters Patent is hereby corrected as shown below:

On the Title Page Item [62] should read

Divisional of application 11/483,050, filed on Jul. 7, 2006, now Pat. No. 7,931,584, which is a continuation of PCT/JP2005/0016 filed on Jan. 1, 2005

Signed and Sealed this
Fourteenth Day of October, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,709,329 B2 | Page 1 of 1 |
| APPLICATION NO. | : 13/080999 | |
| DATED | : April 29, 2014 | |
| INVENTOR(S) | : Akagi et al. | |

It is certified that error appears in the above-identified patent and that said Letters Patent is hereby corrected as shown below:

On the Title Page Item [62] should read

Divisional of application 11/483,050, filed on Jul. 7, 2006, now Pat. No. 7,931,584, which is a continuation of PCT/JP2005/00116 filed on Jan. 1, 2005

This certificate supersedes the Certificate of Correction issued October 14, 2014.

Signed and Sealed this
Sixteenth Day of December, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,709,329 B2
APPLICATION NO.  : 13/080999
DATED            : April 29, 2014
INVENTOR(S)      : Akagi et al.

Page 1 of 1

It is certified that error appears in the above-identified patent and that said Letters Patent is hereby corrected as shown below:

On the Title Page Item [62] should read

Divisional of application 11/483,050, filed on Jul. 7, 2006, now Pat. No. 7,931,584, which is a continuation of PCT/JP2005/00116 filed on Jan. 7, 2005

This certificate supersedes the Certificates of Correction issued October 14, 2014 and December 16, 2014.

Signed and Sealed this
Twenty-fourth Day of March, 2015

Michelle K. Lee
*Director of the United States Patent and Trademark Office*